US011627750B2

(12) United States Patent
Winkle et al.

(10) Patent No.: US 11,627,750 B2
(45) Date of Patent: Apr. 18, 2023

(54) METHOD FOR EXTRACTING MYCOTOXINS FROM GRAIN, OTHER FOOD PRODUCTS AND ANIMAL FEED

(71) Applicant: R-Biopharm Aktiengesellschaft, Darmstadt (DE)

(72) Inventors: Johannes Winkle, Hirschberg (DE); Dirk Blödorn, Frankfurt am Main (DE); Kholoud Zaid, Darmstadt (DE); Markus Lacorn, Oestrich-Winkel (DE)

(73) Assignee: R-BIOPHARM AKTIENGESELLSCHAFT, Darmstadt (DE)

( * ) Notice: Subject to any disclaimer, the term of this patent is extended or adjusted under 35 U.S.C. 154(b) by 1066 days.

(21) Appl. No.: 16/318,178

(22) PCT Filed: Jun. 21, 2017

(86) PCT No.: PCT/EP2017/000721
§ 371 (c)(1),
(2) Date: Jan. 16, 2019

(87) PCT Pub. No.: WO2018/014988
PCT Pub. Date: Jan. 25, 2018

(65) Prior Publication Data

US 2019/0281870 A1 Sep. 19, 2019

(30) Foreign Application Priority Data

Jul. 18, 2016 (EP) .................................... 16001588

(51) Int. Cl.
*A23K 10/30* (2016.01)
*A23L 5/20* (2016.01)
(Continued)

(52) U.S. Cl.
CPC ................ *A23L 5/23* (2016.08); *A23K 10/30* (2016.05); *A23L 7/197* (2016.08);
(Continued)

(58) Field of Classification Search
CPC ... A23L 5/23; A23L 7/197; A23L 5/20; A23L 5/27; A23K 10/30; A23K 30/00;
(Continued)

(56) References Cited

U.S. PATENT DOCUMENTS

2005/0165076 A1* 7/2005 Ammermann ....... A01N 43/653
514/383
2009/0110563 A1* 4/2009 Takita ..................... C02F 1/441
417/399

(Continued)

FOREIGN PATENT DOCUMENTS

CA 2962710 A1 * 4/2016 ............... G01N 1/40
IT M1931079 * 11/1994 ................ F03B 3/02

(Continued)

OTHER PUBLICATIONS

Wacoo et al, "Methods for Detection of Aflatoxins in Agricultural Food Crops", Hindawi Publishing Corporation, Journal of Applied Chemistry, vol. 2014, Article ID 706291, Published Aug. 25, 2014. (Year: 2014).*

(Continued)

*Primary Examiner* — Joseph W Drodge
(74) *Attorney, Agent, or Firm* — Buchanan Ingersoll & Rooney PC

(57) ABSTRACT

The invention relates to a method for extracting mycotoxins from grain and other food products or from feed and its subsequent quantification. Fields of application are the food industry, the animal feed industry or biotechnology. The objective of the present invention is to develop an extraction method with which it is possible to uniformly extract
(Continued)

mycotoxins with different dissolving properties. It was found that with the aid of aqueous, buffered naphthyl and/or phenyl compounds or their heterocyclical analogues, both hydrophobic and hydrophilic mycotoxins can be extracted. The method according to the invention is characterized in that the buffered solutions of naphthyl and/or phenyl compounds and/or their heterocyclical analogues, which carry at least one sulphonic acid or at least one carbonate acid group, are brought into contact with the grain or other food products or animal feed, the aqueous solution is then separated and the content of the extracted mycotoxins in the aqueous solution is determined.

12 Claims, 1 Drawing Sheet

(51) Int. Cl.

| | |
|---|---|
| ***B01D 15/38*** | (2006.01) |
| ***G01N 33/02*** | (2006.01) |
| ***G01N 33/10*** | (2006.01) |
| ***G01N 33/53*** | (2006.01) |
| ***A23L 7/10*** | (2016.01) |
| *G01N 1/40* | (2006.01) |

(52) U.S. Cl.
CPC ......... *B01D 15/3809* (2013.01); *G01N 33/02* (2013.01); *G01N 33/10* (2013.01); *G01N 33/53* (2013.01); *A23V 2002/00* (2013.01); *G01N 2001/4061* (2013.01)

(58) Field of Classification Search
CPC .. B01D 15/3809; B01D 11/02; B01D 11/028; B01D 11/0288; B01D 15/08; B01D 15/38; B01D 15/3823; G01N 33/02; G01N 33/10; G01N 33/53; G01N 2001/4061; G01N 30/02; G01N 2030/022; G01N 2030/062; A23V 2002/00; A23V 2300/14; B01J 20/24; B01J 2220/4812; B01J 2220/4868; B01J 2220/54
See application file for complete search history.

(56) References Cited

U.S. PATENT DOCUMENTS

| | | | | |
|---|---|---|---|---|
| 2009/0124678 A1* | 5/2009 | Semar | A01N 43/653 | 514/383 |
| 2009/0269859 A1* | 10/2009 | Liu | B01D 15/3809 | 436/541 |
| 2013/0203613 A1* | 8/2013 | Burmeister | B01L 3/502715 | 506/18 |
| 2014/0356978 A1 | 12/2014 | Jabour et al. | | |
| 2016/0278405 A1* | 9/2016 | Sarver, Jr. | A23L 5/273 | |
| 2017/0099862 A1 | 4/2017 | Binder et al. | | |

FOREIGN PATENT DOCUMENTS

| | | |
|---|---|---|
| WO | 2014114982 A1 | 7/2014 |
| WO | 2015188205 A1 | 12/2015 |
| WO | 2016057044 A1 | 4/2016 |

OTHER PUBLICATIONS

English Translated Abstract of Fiorenzo et al Patent Publication ITM1931079, Published Nov. 26, 1994. (Year: 1994).*
International Search Report (PCT/ISA/210) dated Aug. 28, 2017, by the European Patent Office as the International Searching Authority for International Application No. PCT/EP2017/000721.
Written Opinion (PCT/ISA/237) dated Aug. 28, 2017, by the European Patent Office as the International Searching Authority for International Application No. PCT/EP2017/000721.

* cited by examiner

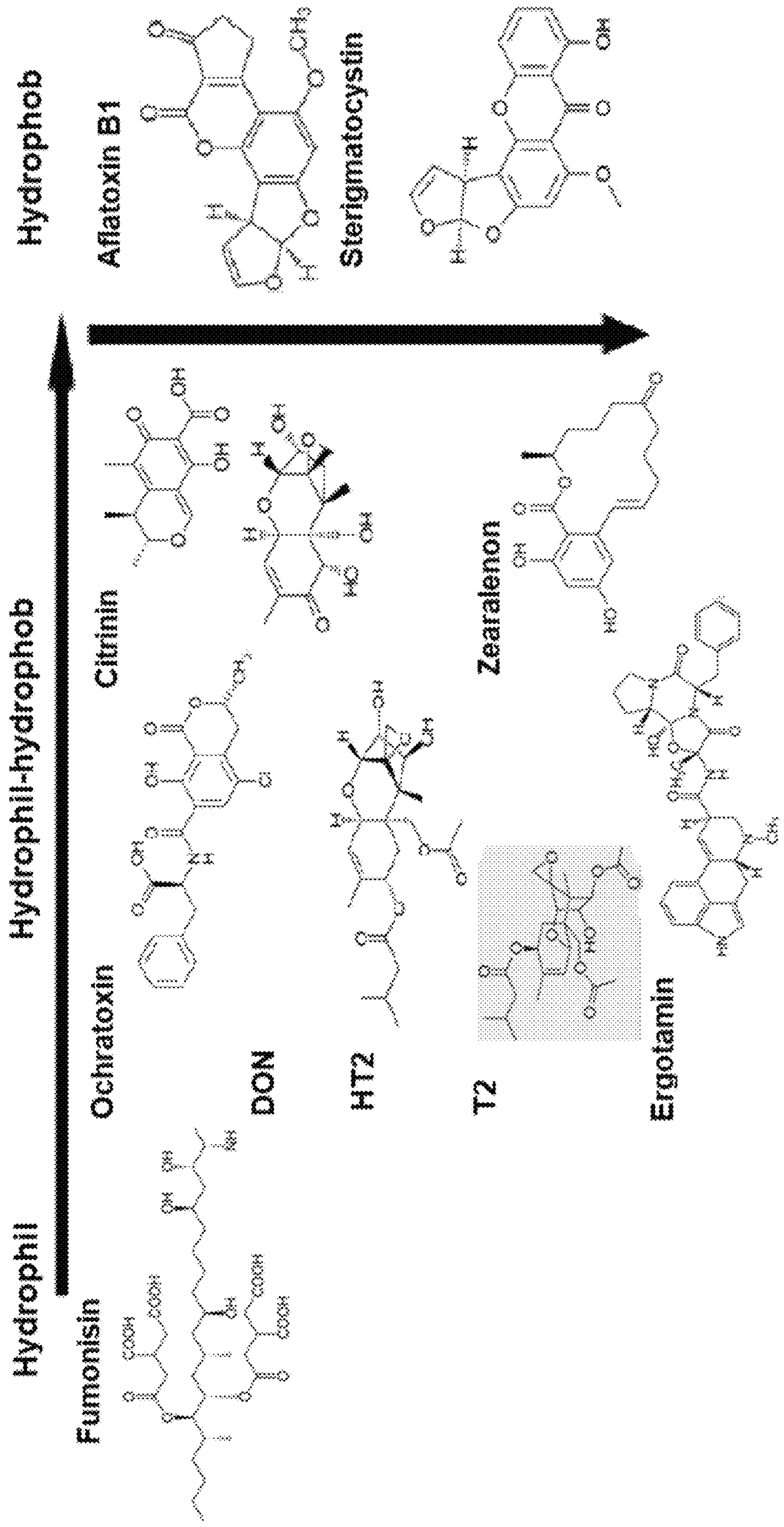
Fumonisin
Ochratoxin
DON
HT2
T2
Ergotamin
Citrinin
Zearalenon
Aflatoxin B1
Sterigmatocystin

METHOD FOR EXTRACTING MYCOTOXINS FROM GRAIN, OTHER FOOD PRODUCTS AND ANIMAL FEED

CROSS REFERENCE TO RELATED APPLICATIONS

This application is a national stage of international application no. PCT/EP2017/000721, filed on Jun. 21, 2017, and claims the benefit of priority under 35 USC 119 of EP application no. 16001588.9, filed on Jul. 18, 2016.

FIELD OF THE INVENTION

The invention relates to a method for extracting mycotoxins from grain and other food products or from animal feed and its subsequent quantification. Fields of application are the food industry, the animal feed industry or biotechnology.

BACKGROUND TO THE INVENTION

Mycotoxins are secondary metabolic products formed by mould fungi that can already have a toxic effect among vertebrae even in tiny quantities. Currently, around 200 different mycotoxins are known, which are formed by over 300 types of fungus. The term “mycotoxins” comprises a series of chemical compounds with different structures and effects, which can be classified as the following substance groups: Aflatoxins, ochratoxins, trichothecenes such as deoxynivalenol, fumonisins, alternaria toxins, fusarium toxins, ergot alkaloids.

Of particular importance in the food and animal feed industries are mycotoxins of the aflatoxin group, the fumonisin group, ochratoxin A, deoxynivalenol (DON), HT-2-toxin (or HT2), T-2-toxin (or T2) and zearalenone. Due to their extremely high hazard potential and broad dissemination, the tiniest quantities in food products or animal feed can already acutely or chronically impair the health of humans and animals. For this reason, legislators worldwide have set limit values for the different mycotoxins in different matrices, which are valid at national level. As an example, reference is made to EU directive 1881 from 2006. Further, in this context, minimal standards for test systems (e.g. ELISA) were determined in the EU by directive 519 from 2014. For this reason, there is an extraordinarily high level of interest in examining food products or animal feed for any mycotoxin contamination. Here, the fact has proven to be problematic in the past that the aforementioned mycotoxins are extremely heterogeneous in terms of their molecular structure, and therefore have a wide range of properties such as different dissolving properties. Thus, the hydrophobic aflatoxins are indissoluble in water, while by contrast, the fumonisins and deoxynivalenol are soluble in water (FIG. 1). For this reason, aflatoxins must be extracted from a sample using water-methanol or water-ethanol mixtures. The other mycotoxins, such as T2 and HT2 (FIG. 1) are at a medium level with regard to their polarity and extractability, although they also require solvents such as methanol for extraction.

State of the Art

To date, mycotoxins have been extracted using organic solvents such as ethanol, acetonitrile or methanol. However, large quantities of organic solvents are created during the process, which must then be disposed of. As an alternative, methods have been developed in which certain mycotoxins can be extracted through the addition of specific substances such as cyclodextrins, components containing proteins (e.g. cattle serum albumin) or solubilising agents (e.g. non-ionic tensides such as triton or Brij). Such methods without organic solvents have frequently been patented in recent years (US 2014/0356978; WO 2015/188205; WO 2016/057044). However, with regard to extractions without organic solvents, the extraction of ochratoxin is either not described or requires the use of a special buffer due to the carboxyl function contained in the molecule (Mishra et al., 2016, Food Add.Contam. 33: 500-508). An extraction method for all relevant mycotoxins has not yet been described.

Due to the aforementioned disadvantages, these methods are not the agent of choice in order to analyse food products such as grain samples for the presence of a wide range of mycotoxins quickly, simply, in an environmentally friendly manner and at low cost.

Goal and Objective of the Invention

The goal of the invention is to extract a wide range of mycotoxins (FIG. 1) from food products and animal feed in the most uniform manner possible with a single extraction agent.

From this, the objective of the present invention is derived of developing an extraction method with which it is possible to uniformly extract mycotoxins with different dissolving properties.

In particular, this results in the objective of extracting the mycotoxins aflatoxin, deoxynivalenol, ochratoxin A, zearalenone, fumonisin and T2/HT2 from grain (maize, wheat, rye, oats, barley and their relatives from the triticeae tribe), animal feed, nuts, soya, maize gluten and rice, as well as figs, dates, raisins and pistachios, and then to quantify them.

This objective is attained by means of a method according to claim 1. Further possible embodiments are presented in the subclaims, the description and the examples.

Nature of the Invention

Surprisingly, it has been found that with the aid of aqueous, buffered naphthyl and/or phenyl compounds or their heterocyclical analogues, both hydrophobic and hydrophilic mycotoxins can be extracted.

The method according to the invention is characterized in that the buffered solutions of naphthyl and/or phenyl compounds and/or their heterocyclical analogues, which carry at least one sulphonic acid or at least one carbonate acid group, are brought into contact with the grain or other food products or animal feed, the aqueous solution is then separated and the content of the extracted mycotoxins in the aqueous solution is determined.

According to the invention, naphthyl or phenyl compounds or their heterocyclical analogues of the general formula I are used individually or as a mixture in order to particularly effectively extract mycotoxins of a wide range of different groups.

Formula I

in which X, R1 and R2 have the following meaning:

X=naphthyl or phenyl residue or its heterocyclical analogues

R1=at least one sulphonic acid group or at least one carbonic acid group

R2=unsubstituted or selected from a functional group of hydroxy, alkyl, alkoxy, amino, sulfhydryl, halogen and thioether, which are arranged in the o, m or p position in relation to the acid group in the molecule, whereby α-amino acids are excluded.

Examples are listed below that are capable of extracting mycotoxins of a wide range of different groups:

1,5-naphthyl disulphonic acid
2,6-naphthyl disulphonic acid
4-hydroxyphenylsulphonic acid
Benzenesulphonic acid
4-methyl benzenesulphonic acid
Benzene-1,3-disulphonic acid
1-naphthol-3,6-disulphonic acid
3-sulphobenzoic acid
4-sulphobenzoic acid
2-hydroxybenzoic acid
2,6-dihydroxybenzoic acid
2,5-dihydroxybenzoic acid
2,4-dihydroxybenzoic acid
3,4-dihydroxybenzoic acid
3,5-dihydroxybenzoic acid
2-hydroxy-5-sulphobenzoic acid The sole but also combined use of 1,5-naphtyldisulphonic acid, 2,6-naphthyldisulphonic acid and/or p-hydroxyphenyl sulphonic acid emerged as being particularly advantageous.

The result aqueous supernatant, which contains the extracted mycotoxins, is then separated and used for analysis. In this way, the determination or further purification of the mycotoxins can be achieved, for example with the aid of enzymatic, enzyme immunological, chromatographically supported and/or immuno-affinity chromatographic methods.

Certified reference materials (Table 1) are used for all tests described below. For each mycotoxin, a blank sample and a contaminated reference sample are measured.

TABLE 1

Certified mycotoxin reference materials for testing the extraction efficiency of the claimed method

| Mycotoxin (matrix) | Reference value* | Certified material Name** |
|---|---|---|
| Aflatoxins | n.d. | AC 215 |
| (maize) | 31.2 ± 3.1 µg/kg | AC 295 |
| Ochratoxin | n.d. | OC 853 |
| (maize) | 12.3 ± 1.3 µg/kg | OC 866 |
| Deoxynivalenol | n.d. | DW 100 |
| (wheat) | 2.1 ± 0.3 mg/kg | DW 174 |
| Fumonisins | n.d. | FC 400 |
| (maize) | 0.5 ± 0.07 mg/kg | FC 458 |
| Zearalenone | n.d. | ZC 300 |
| (maize) | 472.1 ± 65.6 µg/kg | ZC 321 |
| T2/HT2 | n.d. | TC 978 |
| (maize) | 255.7 ± 18 µd/kg T2 and 681.1 ± 45.8 µg/kg HT2 | TC 982 |

*not detected using HPLC; see certificates from Trilogy for more detailed explanations, e.g. verification limit of the method used
**Materials from Trilogy (Washington, MO, USA) were used The invention will now be explained with reference to the determination of aflatoxin in maize. The reference extraction method provides for a sample weigh-in of 1 g, which is extracted with 5 ml 70% methanol in water for 10 min while shaking (Table 2). After centrifugation or filtration, the supernatant is diluted 1:7 with distilled water (e.g. 100 µL extract+600 µL water) and the aflatoxin content is quantified in a standard commercial ELISA. The RIDASCREEN® Aflatoxin Total (art. no. 4701, R-Biopharm AG, Darmstadt, see also Table 2) is used. The basis is the antigen-antibody reaction. The recesses in the microtitre plates are coated against anti-aflatoxin antibodies with capture antibodies. Calibrators or extracted sample solution, enzyme-marked aflatoxin (enzyme conjugate) and anti-aflatoxin antibodies are added. Free and enzyme-marked aflatoxin compete for the aflatoxin antibody binding sites. At the same time, the anti-aflatoxin antibodies are also bound by the immobilised capture antibodies. Non-bound enzyme-marked aflatoxin is then removed again in a washing step. Verification is conducted by adding substrate/chromogenic solution. Bound enzyme conjugate converts the chromogen into a blue end product. The addition of the stop reagent leads to a colour change from blue to yellow. The measurement is conducted photometrically at 450 nm; the measured optical density (OD) of the solution is conversely proportional to the aflatoxin concentration in the sample.

TABLE 2

Applied reference extraction and ELISA system used to compare the extraction efficiency of the claimed methods

| Mycotoxin (matrix) | Reference extraction | ELISA |
|---|---|---|
| Aflatoxins (maize) | 1 g sample + 5 ml 70% methanol in water; dilution 1:7 with water | R4701 (RIDASCREEN ® Aflatoxin Total) |
| Ochratoxin (maize) | 1 g sample + 5 ml 130 mM $NaHCO_3$ (pH 8.1); dilution 1:4 with water | R1311 (RIDASCREEN ® Ochratoxin A 30/15 |
| Deoxynivalenol (wheat) | 1 g sample + 5 ml water; dilution 1:10 with water | R5906 (RIDASCREEN ® DON) |
| Fumonisins (maize) | 1 g sample + 5 ml 70% methanol in water; dilution 1:14 with water | R3401 (RIDASCREEN ® Fumonisin) |
| Zearalenone (maize) | 1 g sample + 5 ml 70% methanol in water; dilution with buffer | R1401 (RIDASCREEN ® Zearalenone) |
| T2/HT2 (maize) | 1 g sample + 5 ml 70% methanol in water; dilution 1:20 with water | R3805 (RIDASCREEN ® T2/HT2 Toxin |

As an example, a preferred method for the extraction of aflatoxin from maize is described below. For this purpose, 1 g of homogenised maize sample with 5 ml of a solution consisting of 250 mM 1,5-naphthyl disulphonic acid buffered to pH 8 is mixed with 100 mM tris-(hydroxymethyl)-aminomethane (tris), shaken for 10 min and centrifuged or filtered. The clear supernatant is diluted 1:7 with distilled water and measured in the ELISA as already described above.

The results are shown in Table 3. Here, it should be noted that for comparability reasons, the results are given as a "signal reduction in %". The signal reduction results from the competitive format of the ELISA as a test system. The extraction yield should be evaluated as a comparison between the new, claimed method and the established reference extraction. A high analyte concentration in the extract (caused by a high extraction yield) leads to a reduction of the measurement signal ($OD_{450\ nm}$). The signal reduction in [%] is calculated as follows:

$$\text{Signal reduction}[\%]=100-(OD_{positive\ sample}/OD_{negative\ sample}\times 100)$$

TABLE 3

Extraction yield of aflatoxin from maize using the claimed substance 1,5-naphthyl disulphonic acid (in tris buffer pH 8.0) compared to the reference extraction. The OD value was calculated in the commercially available ELISA RIDASCREEN ® Aflatoxin Total.

| | Reference extraction | 250 mM 1,5-NDS + 100 mM tris pH 8.0 |
|---|---|---|
| $OD_{Blank}$ | 1.591 | 1.966 |
| $OD_{Positive}$ | 0.474 | 0.525 |
| Signal reduction [%] | 71 | 73 |

If one compares the values of the reference extraction with those of the claimed extraction, it becomes clear that these are very similar. Aflatoxin was thus successfully quantitatively extracted from the matrix maize using the claimed method. Slight differences in the OD values, above all of the blank samples, can be explained by secondary effects of the claimed substances in the ELISA measurement system. Through interactions, the competition for antibody binding sites between the aflatoxin from the extract (sample) and aflatoxin-enzyme conjugate is slightly disrupted. This is also the reason why no concentration values have been determined, but the results are instead given as "signal reduction [%]". This would create a false picture, since the influencing of the ELISA is not a part of the claimed extraction. The ELISA systems can accordingly be set to such substances, so that the accuracy of the measurement system is provided.

Independently of the example given above, it is however also possible to study other samples from the food or animal feed area such as wheat, rye, oats, barley and their relatives from the triticeae tribe, animal feed, nuts, soya, maize gluten and rice. Furthermore, figs, dates, raisins and pistachios are also of interest.

Equally, the extraction is not limited to the above aflatoxins. Thus, it is also possible to extract deoxynivalenol, ochratoxin A, zearalenone, fumonisin and T2/HT2 with the method according to the invention. Equally, other toxins such as ergot alkaloids, citrinin and sterigmatocystin can be extracted with the method according to the invention.

Studies have shown that the effectiveness of the method is positively influenced by a suitable buffer system. Thus, the aqueous solution of naphthyl and/or phenyl compounds and/or their heterocyclical analogues should be buffered in the range of pH 5-10. Here, buffers containing tris-(hydroxy methyl)-aminomethane (tris) and "Imidazol" are preferred in the region of pH 7.5-8.5 (see example in Table 3). The "Imidazol" buffer was prepared by mixing the isopropylimidazol and Imidazol hydrochloride in the corresponding proportions. Other buffer systems such as phosphate and EPPS N-(2-hydroxyethyl)-piperazine-N'-(3-propane sulphonic acid) are also possible, but can have different extraction results depending on the concentration and mycotoxin.

An extraction method is also possible in which aromatic phenyl or naphthyl compounds are used with at least on position substituted with nitrogen.

The method has the advantage over the extraction methods known to date that all important mycotoxins can be extracted efficiently and almost entirely from relevant food product matrices with an environmentally friendly, aqueous extraction agent. Unlike the standard methods, the analysis of several different mycotoxins no longer requires separate sample weigh-ins and individual extraction agents, but simply a single sample weigh-in and universal extraction with the claimed method. This results in significant time and material savings for the user of this new method, which leads to a cost reduction and the avoidance of exposure to solvents from the extraction agents of standard methods, which are harmful to health.

The invention will now be explained in greater detail with reference to illustrative embodiments.

Illustrative Embodiments

EXAMPLE 1

TABLE 4

Extraction yield of aflatoxin from maize using the claimed substances 1,5-naphthyl disulphonic acid (1,5-NDS, 250 mM) using different buffers (100 mM) and pH values compared to reference extraction (ref., see also Table 2). The OD value was calculated in the commercially available ELISA RIDASCREEN ® Aflatoxin Total.

| | Ref. | 1,5-NDS Tris pH 8.0 | 1,5-NDS Tris pH 8.5 | 1,5-NDS Imidazol pH 8.0 | 1,5-NDS Imidazol pH 8.5 |
|---|---|---|---|---|---|
| $OD_{Blank}$ | 1.591 | 1.966 | 1.917 | 1.684 | 1.578 |
| $OD_{Positive}$ | 0.474 | 0.525 | 0.491 | 0.401 | 0.326 |
| Signal reduction [%] | 71 | 73 | 74 | 76 | 79 |

EXAMPLE 2

TABLE 5

Extraction yield of aflatoxin from maize using the claimed substances 2,6-naphthyl disulphonic acid (2,6-NDS, 125 mM) using different buffers (100 mM) and pH values compared to reference extraction (ref., see also Table 2). The OD value was calculated in the commercially available ELISA RIDASCREEN ® Aflatoxin Total.

| | Ref. | 2,6-NDS Tris pH 8.0 | 2,6-NDS Tris pH 8.5 | 2,6-NDS Imidazol pH 8.0 | 2,6-NDS Imidazol pH 8.5 |
|---|---|---|---|---|---|
| $OD_{Blank}$ | 1.505 | 1.686 | 1.711 | 1.654 | 1.645 |
| $OD_{Positive}$ | 0.377 | 0.435 | 0.356 | 0.403 | 0.393 |
| Signal reduction [%] | 75 | 74 | 79 | 76 | 76 |

EXAMPLE 3

TABLE 6

Extraction yield of aflatoxin from maize using the claimed substances 1,5-naphthyl disulphonic acid (1,5-NDS, 250 mM) using different buffers (100 mM) and pH values compared to reference extraction (ref., see also Table 2). The OD value was calculated in the commercially available ELISA RIDASCREEN ® DON.

| | Ref. | 1,5-NDS Tris pH 8.0 | 1,5-NDS Tris pH 8.5 | 1,5-NDS Imidazol pH 8.0 | 1,5-NDS Imidazol pH 8.5 |
|---|---|---|---|---|---|
| $OD_{Blank}$ | 2.440 | 2.682 | 2.722 | 2.649 | 2.638 |
| $OD_{Positive}$ | 0.738 | 0.795 | 0.842 | 0.744 | 0.811 |
| Signal reduction [%] | 70 | 70 | 69 | 72 | 69 |

EXAMPLE 4

TABLE 7

Extraction yield of aflatoxin from maize using the claimed substances 2,6-naphthyl disulphonic acid (2,6-NDS, 125 mM) using different buffers (100 mM) and pH values compared to reference extraction (ref., see also Table 2). The OD value was calculated in the commercially available ELISA RIDASCREEN ® DON.

| | Ref. | 2,6-NDS Tris pH 8.0 | 2,6-NDS Tris pH 8.5 | 2,6-NDS Imidazol pH 8.0 | 2,6-NDS Imidazol pH 8.5 |
|---|---|---|---|---|---|
| $OD_{Blank}$ | 2.463 | 2.694 | 2.667 | 2.610 | 2.657 |
| $OD_{Positive}$ | 0.886 | 0.923 | 0.923 | 0.871 | 0.906 |
| Signal reduction [%] | 64 | 66 | 65 | 67 | 66 |

EXAMPLE 5

TABLE 8

Extraction yield of aflatoxin from maize using the claimed substances 1,5-naphthyl disulphonic acid (1,5-NDS, 250 mM) using different buffers (100 mM) and pH values compared to reference extraction (ref., see also Table 2). The OD value was calculated in the commercially available ELISA RIDASCREEN ® Ochratoxin A 30/15.

| | Ref. | 1,5-NDS Tris pH 8.0 | 1,5-NDS Tris pH 8.5 | 1,5-NDS Imidazol pH 8.0 | 1,5-NDS Imidazol pH 8.5 |
|---|---|---|---|---|---|
| $OD_{Blank}$ | 1.551 | 1.447 | 1.374 | 1.479 | 1.277 |
| $OD_{Positive}$ | 0.305 | 0.338 | 0.306 | 0.366 | 0.296 |
| Signal reduction [%] | 80 | 77 | 78 | 75 | 77 |

EXAMPLE 6

TABLE 9

Extraction yield of ochratoxin A from maize using the claimed substances 2,6-naphthyl disulphonic acid (2,6-NDS, 125 mM) using different buffers (100 mM) and pH values compared to reference extraction (ref., see also Table 2). The OD value was calculated in the commercially available ELISA RIDASCREEN ® Ochratoxin A 30/15.

| | Ref. | 2,6-NDS Tris pH 8.0 | 2,6-NDS Tris pH 8.5 | 2,6-NDS Imidazol pH 8.0 | 2,6-NDS Imidazol pH 8.5 |
|---|---|---|---|---|---|
| $OD_{Blank}$ | 1.551 | 1.602 | 1.462 | 1.425 | 1.374 |
| $OD_{Positive}$ | 0.305 | 0.407 | 0.309 | 0.324 | 0.263 |
| Signal reduction [%] | 80 | 75 | 79 | 77 | 81 |

EXAMPLE 7

TABLE 10

Extraction yield of zearalenone from maize using the claimed substances 1,5-naphthyl disulphonic acid (1,5-NDS, 250 mM) or 2,6-naphthyl disulphonic acid using different buffers (2,6-NDS, 100 mM) and pH values compared to reference extraction (ref., see also Table 2). The OD value was calculated in the commercially available ELISA RIDASCREEN ® zearalenone.

| | Ref. | 1,5-NDS Tris pH 8.0 | 1,5-NDS Imidazol pH 8.5 | 2,6-NDS Tris pH 8.0 | 2,6-NDS Imidazol pH 8.0 |
|---|---|---|---|---|---|
| $OD_{Blank}$ | 3.093 | 2.594 | 2.540 | 2.403 | 2.214 |
| $OD_{Positive}$ | 0.227 | 0.355 | 0.268 | 0.245 | 0.301 |
| Signal reduction [%] | 93 | 86 | 89 | 90 | 86 |

EXAMPLE 8

TABLE 11

Extraction yield of fumonisin from maize using the claimed substances 1,5-naphthyl disulphonic acid (1,5-NDS, 50 mM) or 2,6-naphthyl disulphonic acid using different buffers (2,6-NDS, 100 mM) and pH values compared to reference extraction (ref., see also Table 2). The OD value was calculated in the commercially available ELISA RIDASCREEN ® fumonisin.

| | Ref. | 1,5-NDS Tris pH 8.0 | 1,5-NDS Imidazol pH 8.0 | 2,6-NDS Tris pH 8.0 | 2,6-NDS Imidazol pH 8.0 |
|---|---|---|---|---|---|
| $OD_{Blank}$ | 1.193 | 0.719 | 0.762 | 0.874 | 0.881 |
| $OD_{Positive}$ | 0.339 | 0.174 | 0.151 | 0.202 | 0.188 |
| Signal reduction [%] | 72 | 76 | 80 | 77 | 79 |

EXAMPLE 9

TABLE 12

Extraction yield of T2 and HT2 from maize using the claimed substances 1,5-naphthyl disulphonic acid (1,5-NDS, 250 mM) or 2,6-naphthyl disulphonic acid using different buffers (2,6-NDS, 100 mM) and pH values compared to reference extraction (ref., see also Table 2). The OD value was calculated in the commercially available ELISA RIDASCREEN ® T2/HT2.

| | Ref. | 1,5-NDS Tris pH 8.0 | 1,5-NDS Imidazol pH 8.0 | 2,6-NDS Tris pH 8.0 | 2,6-NDS Imidazol pH 8.0 |
|---|---|---|---|---|---|
| $OD_{Blank}$ | 1.676 | 0.947 | 0.921 | 0.868 | 0.799 |
| $OD_{Positive}$ | 0.467 | 0.289 | 0.282 | 0.270 | 0.265 |
| Signal reduction [%] | 72 | 69 | 69 | 69 | 67 |

EXAMPLE 10

TABLE 13

Extraction yield of aflatoxin from maize using the claimed substances 1,5-naphthyl disulphonic acid (1,5-NDS, 250 mM) or 2,6-naphthyl disulphonic acid (2,6-NDS, 100 mM) and pH values compared to reference extraction (ref., see also Table 2). The OD value was calculated in the commercially available ELISA RIDASCREEN ® Aflatoxin Total.

| | Ref. | 1,5-NDS Phosphate 200 mM pH 8.0 | 1,5-NDS Epps* 100 mM pH 8.5 | 2,6-NDS Phosphate 25 mM pH 8.0 | 2,6-NDS Phosphate 75 mM pH 8.5 |
|---|---|---|---|---|---|
| $OD_{Blank}$ | 1.487 | 1.542 | 1.607 | 1.474 | 1.445 |
| $OD_{Positive}$ | 0.326 | 0.303 | 0.350 | 0.339 | 0.350 |
| Signal reduction [%] | 78 | 80 | 78 | 77 | 76 |

*(N-(2-hydroxyethyl)-piperazine-N'-(3-propane sulphonic acid)

EXAMPLE 11

TABLE 14

Extraction yield of aflatoxin from maize using the claimed substance 1,5-naphthyl disulphonic acid in different concentrations at pH 8.0 (5 mM phosphate) compared to reference extraction (ref., see also Table 2). The OD value was calculated in the commercially available ELISA RIDASCREEN ® Aflatoxin Total.

| | Ref. | 300 mM | 200 mM | 100 mM | 50 mM | 10 mM |
|---|---|---|---|---|---|---|
| $OD_{Blank}$ | 1.320 | 1.516 | 1.611 | 1.601 | 1.596 | 1.601 |
| $OD_{Positive}$ | 0.325 | 0.309 | 0.373 | 0.452 | 0.752 | 0.920 |
| Signal reduction [%] | 75 | 80 | 77 | 72 | 53 | 43 |

EXAMPLE 12

TABLE 15

Extraction yield of aflatoxin from maize using the claimed substance 2,6-naphthyl disulphonic acid in different concentrations at pH 8.0 (5 mM phosphate) compared to reference extraction (ref., see also Table 2). The OD value was calculated in the commercially available ELISA RIDASCREEN ® Aflatoxin Total.

| | Ref. | 100 mM | 75 mM | 50 mM | 10 mM | 5 mM |
|---|---|---|---|---|---|---|
| $OD_{Blank}$ | 1.544 | 1.860 | 1.854 | 1.881 | 1.962 | 1.973 |
| $OD_{Positive}$ | 0.438 | 0.489 | 0.521 | 0.620 | 1.101 | 1.051 |
| Signal reduction [%] | 72 | 74 | 72 | 67 | 44 | 47 |

EXAMPLE 13

TABLE 16

Extraction yield of deoxynivalenol, fumonisin and zearalenone (for matrices see Table 1) using the claimed substance 4-hydroxyphenyl sulphonic acid (375 mM; 4-OH-PSN) with the addition of 50 mM phosphate (pH 8.0) compared to the reference extraction (ref., see also Table 2). The OD value was calculated in the commercially available ELISA RIDASCREEN ® series (see Table 2).

| | DON ref. | DON 4-OH-PSN | Fumo* ref. | Fumo* 4-OH-PSN | Zea* ref. | Zea* 4-OH-PSN |
|---|---|---|---|---|---|---|
| $OD_{Blank}$ | 2.337 | 2.577 | 1.261 | 0.814 | 3.012 | 2.338 |
| $OD_{Positive}$ | 0.786 | 0.824 | 0.398 | 0.195 | 0.195 | 0.294 |
| Signal reduction [%] | 66 | 68 | 68 | 76 | 94 | 87 |

*DON, deoxynivalenol; fumo, fumonisin; zea, zearalenone

EXAMPLE 14

TABLE 17

Extraction yield of aflatoxin, ochratoxin and T2/HT2 (for matrices see Table 1) using the claimed substance 4-hydroxyphenyl sulphonic acid (375 mM; 4-OH-PSN) with the addition of 50 mM phosphate (pH 8.0) compared to the reference extraction (ref., see also Table 2). The OD value was calculated in the commercially available ELISA RIDASCREEN ® series (see Table 2).

| | Afla* ref. | Afla* 4-OH-PSN | OTA* ref. | OTA* 4-OH-PSN | T2/HT2 ref. | T2/HT2 4-OH-PSN |
|---|---|---|---|---|---|---|
| $OD_{Blank}$ | 1.701 | 1.821 | 1.551 | 1.557 | 1.889 | 0.965 |
| $OD_{Positive}$ | 0.451 | 0.673 | 0.305 | 0.308 | 0.525 | 0.342 |
| Signal reduction [%] | 73 | 63 | 80 | 80 | 72 | 65 |

*Afla, aflatoxin; OTA, ochratoxin

EXAMPLE 15

TABLE 18

Extraction yield of aflatoxin from maize using the claimed substance 4-naphthyl disulphonic acid in different concentrations at pH 8.0 (5 mM phosphate) compared to reference extraction (ref., see also Table 2). The OD value was calculated in the commercially available ELISA RIDASCREEN ® Aflatoxin Total.

| | Ref. | 600 mM | 500 mM | 400 mM | 300 mM | 200 mM | 100 mM |
|---|---|---|---|---|---|---|---|
| $OD_{Blank}$ | 1.485 | 1.692 | 1.707 | 1.712 | 1.722 | 1.692 | 1.649 |
| $OD_{Positive}$ | 0.440 | 0.512 | 0.533 | 0.547 | 0.568 | 0.676 | 0.855 |
| Signal reduction [%] | 70 | 70 | 69 | 68 | 67 | 60 | 48 |

EXAMPLE 16

TABLE 19

Extraction yield of aflatoxin from maize using the claimed substance 4-naphthyl disulphonic acid in different concentrations at pH 8.0 (5 mM phosphate) compared to reference extraction (ref., see also Table 2). The OD value was calculated in the commercially available ELISA RIDASCREEN ® Ochratoxin A 30/15.

| | Ref. | 600 mM | 500 mM | 400 mM | 300 mM | 200 mM | 50 mM |
|---|---|---|---|---|---|---|---|
| $OD_{Blank}$ | 1.620 | 1.308 | 1.365 | 1.345 | 1.383 | 1.475 | 1.692 |
| $OD_{Positive}$ | 0.239 | 0.264 | 0.229 | 0.264 | 0.241 | 0.267 | 0.309 |
| Signal reduction [%] | 85 | 80 | 83 | 80 | 83 | 82 | 82 |

EXAMPLE 17

TABLE 20

Extraction yield of ochratoxin from maize with combined use of the claimed substances 1,5-naphthyl disulphonic acid (1,5-NDS, 250 mM) and 4-hydroxy phenyl sulphonic acid (different concentrations of 10 mM to 150 mM) at pH 8.0 (5 mM phosphate) compared to reference extraction (ref., see also Table 2). The OD value was calculated in the commercially available ELISA RIDASCREEN ® Ochratoxin A 30/15.

| | | 250 mM 1,5-NDS | | | | | |
|---|---|---|---|---|---|---|---|
| | Ref. | 150 mM | 100 mM | 75 mM | 50 mM | 20 mM | 10 mM |
| $OD_{Blank}$ | 1.551 | 1.120 | 1.231 | 1.360 | 1.352 | 1.494 | 1.495 |
| $OD_{Positive}$ | 0.305 | 0.330 | 0.375 | 0.321 | 0.355 | 0.422 | 0.485 |
| Signal reduction [%] | 80 | 71 | 70 | 76 | 74 | 72 | 68 |

EXAMPLE 18

TABLE 21

Extraction yield of ochratoxin from maize with combined use of the claimed substances 1,5-naphthyl disulphonic acid (1,5-NDS, 250 mM) and 4-hydroxy phenyl sulphonic acid (4-OH-PSN, 50 mM and 75 mM) at different pH values of 7.5 to 9.0 compared to reference extraction (ref., see also Table 2). The OD value was calculated in the commercially available ELISA RIDASCREEN ® Ochratoxin A 30/15.

| | | 250 mM 1,5-NDS | | | | | | | |
|---|---|---|---|---|---|---|---|---|---|
| | | 50 mM 4-OH-PSN | | | | 75 mM 4-OH-PSN | | | |
| | Ref. | pH 7.5 | pH 8.0 | pH 8.5 | pH 9.0 | pH 7.5 | pH 8.0 | pH 8.5 | pH 9.0 |
| $OD_{Blank}$ | 1.551 | 1.342 | 1.249 | 1.210 | 1.265 | 1.244 | 1.223 | 1.139 | 1.108 |
| $OD_{Positive}$ | 0.305 | 0.348 | 0.292 | 0.205 | 0.240 | 0.379 | 0.358 | 0.278 | 0.257 |
| Signal reduction [%] | 80 | 74 | 77 | 83 | 81 | 70 | 71 | 76 | 77 |

EXAMPLE 19

TABLE 22

Extraction yield of ochratoxin from maize with combined use of the claimed substances 2,6-naphthyl disulphonic acid (125 mM) and 4-hydroxy phenyl sulphonic acid (different concentrations of 20 mM to 150 mM) at pH 8.0 (5 mM phosphate) compared to reference extraction (ref., see also Table 2). The OD value was calculated in the commercially available ELISA RIDASCREEN ® Ochratoxin A 30/15.

| | Ref. | 70 mM | 60 mM | 50 mM | 40 mM | 30 mM | 20 mM |
|---|---|---|---|---|---|---|---|
| $OD_{Blank}$ | 1.952 | 1.213 | 1.421 | 1.457 | 1.474 | 1.555 | 1.647 |
| $OD_{Positive}$ | 0.441 | 0.327 | 0.430 | 0.395 | 0.494 | 0.452 | 0.409 |
| Signal reduction [%] | 77 | 73 | 70 | 73 | 67 | 71 | 75 |

EXAMPLE 20

TABLE 23

Extraction yield of ochratoxin from maize with combined use of the claimed substances 2,6-naphthyl disulphonic acid (2,6-NDS, 125 mM) and 4-hydroxy phenyl sulphonic acid (4-OH-PSN, 50 mM and 75 mM) at different pH values of 7.5 to 9.0 compared to reference extraction (ref., see also Table 2). The OD value was calculated in the commercially available ELISA RIDASCREEN ® Ochratoxin A 30/15.

| | | 125 mM 2,6-NDS | | | | | | | |
|---|---|---|---|---|---|---|---|---|---|
| | | 50 mM 4-OH-PSN | | | | 75 mM 4-OH-PSN | | | |
| | Ref. | pH 7.5 | pH 8.0 | pH 8.5 | pH 9.0 | pH 7.5 | pH 8.0 | pH 8.5 | pH 9.0 |
| $OD_{Blank}$ | 1.986 | 1.698 | 1.608 | 1.558 | 1.477 | 1.562 | 1.479 | 1.405 | 1.416 |
| $OD_{Positive}$ | 0.484 | 0.408 | 0.292 | 0.358 | 0.266 | 0.424 | 0.342 | 0.281 | 0.329 |
| Signal reduction [%] | 76 | 76 | 82 | 77 | 82 | 73 | 77 | 80 | 77 |

LEGEND FOR THE FIGURES

FIG. 1: A list of mycotoxins relevant to the food and animal feed industries are shown. Next to the list, their chemical structural formulae and their dissolving properties in an aqueous environment are shown.

The invention claimed is:

1. A method for extracting one or more mycotoxins from grain, a food product or animal feed, wherein an aqueous, buffered solution comprising one or more naphthyl and/or phenyl compounds and/or their heterocyclical analogues of formula I is brought into contact with the grain, food product or animal feed, and the aqueous solution is then separated, formula I

wherein:

X comprises one or more napthyl and/or phenyl compounds and/or their heterocyclical analouges, R1 is at least one sulphonic acid group or at least one carbonic acid group, and R2 is H or selected from a functional group of hydroxy, alkyl, alkoxy, amino, sulfhydryl, halogen and thioether, which are arranged in the o, m or p position in relation to the acid group in the molecule, wherein α-amino acids are excluded.

2. The method of claim 1, wherein X is naphthyl, R1 is disulphonic acid and R2 is hydroxy, or X is phenyl, R1 is sulphonic acid and R2 is hydroxy.

3. The method according to claim 1, wherein the one or more naphthyl and/or phenyl compounds and/or their heterocyclical analogues are selected from the group consisting of 1,5-naphthyl disulphonic acid, 2,6-naphthyl disulphonic acid and hydroxyphenyl sulphonic acid.

4. The method according to claim 1, wherein the one or more naphthyl and/or phenyl compounds and/or their heterocyclical analogues are present in a concentration of 5 to 600 mM of each compound.

5. The method according to claim 1, wherein the one or more naphthyl and/or phenyl compounds and/or their heterocyclical analogues are in a solution, in powder or in tablet form.

6. The method according to claim 1, wherein the buffered, aqueous solution of the one or more naphthyl and/or phenyl compounds and/or their heterocyclical analogues are in the range of pH 5-10.

7. The method according to claim 1, wherein the one or more extracted mycotoxins are subjected to further purification using immunoaffinity chromatography columns.

8. The method according to claim 1, wherein the one or more mycotoxins being extracted are selected from the group consisting of aflatoxin B1, aflatoxin B2, aflatoxin G1, aflatoxin G2, aflatoxin M1, aflatoxin M2, fumonisin B1, fumonisin B2, fumonisin B3, deoxynivalenol, ochratoxin A, zearalenone, T-2, HT-2, citrinin, sterigmatocystin ergot alkaloids and mixtures thereof.

9. The method according to claim 1, wherein the separated aqueous solution is analyzed by determining a concentration of the one or more extracted mycotoxins in the aqueous solution.

10. The method according to claim 9, wherein the concentration of the one or more extracted mycotoxins is determined in an antibody-supported system.

11. The method according to claim 10, wherein the antibody-supported system is an ELISA or a lateral flow systems.

12. The method according to claim 9, wherein the concentration of the one or more extracted mycotoxins is determined in a chromatograph-supported system.

* * * * *